(12) United States Patent
Basheer et al.

(10) Patent No.: US 8,617,866 B2
(45) Date of Patent: Dec. 31, 2013

(54) ROBUST MULTI-ENZYME PREPARATION FOR THE SYNTHESIS OF FATTY ACID ALKYL ESTERS

(76) Inventors: Sobhi Basheer, Sakhnin (IL); Maisa Haj, Shfar-Am (IL); Muhammad Kaiyal, Maker (IL)

( * ) Notice: Subject to any disclaimer, the term of this patent is extended or adjusted under 35 U.S.C. 154(b) by 370 days.

(21) Appl. No.: 12/744,761

(22) PCT Filed: Nov. 13, 2008

(86) PCT No.: PCT/IL2008/001497
§ 371 (c)(1),
(2), (4) Date: Aug. 11, 2010

(87) PCT Pub. No.: WO2009/069116
PCT Pub. Date: Jun. 4, 2009

(65) Prior Publication Data
US 2010/0330629 A1    Dec. 30, 2010

Related U.S. Application Data

(63) Continuation-in-part of application No. 11/946,121, filed on Nov. 28, 2007, now Pat. No. 7,790,429.

(51) Int. Cl.
*C12N 9/20*    (2006.01)

(52) U.S. Cl.
USPC ........... 435/198; 435/134; 554/124; 554/169; 554/174

(58) Field of Classification Search
None
See application file for complete search history.

(56) References Cited

U.S. PATENT DOCUMENTS

| 2003/0175918 A1 | 9/2003 | Basheer |
| 2010/0209982 A1 | 8/2010 | Basheer |

FOREIGN PATENT DOCUMENTS

| EP | 1705238 | 9/2006 |
| KR | 673837 | 11/2005 |
| WO | 2008/084470 | 7/2008 |

OTHER PUBLICATIONS

Basheer et al., May 2008, pp. 1-5, retrieved from the Internet: URL: www.aocs.org/archives/am2008/session.cfm?session=BIO+4+%2F+PRO+4.1%3A+Bioprocessing-Enzymes>; retrieved on May 28, 2009.
Kim et al., Journal of Biotechnology, 131(2):S123 (2007). "Optimization for biodiesel production using a mixture of immobilized *Rhizopus oryzae* and *Candida rugosa* lipases."
Lee et al., Biotechnology and Bioprocess Engineering, 11:522-525 (2006). "Biodiesel production using a mixture of immobilized *Rhizopus oryzae* and *Candida rugosa* Lipases."
Lee et al., Journal of Microbiology and Biotechnology, 18:1927-1931 (2008). "Optimization of the process for biodiesel production using a mixture of immobilized *Rhizopus oryzae* and *Candida rugosa* lipases."
Li et al., Journal of Molecular Catalysis B: Enzymatic, 43:58-62 (2006). "Lipase-catalyzed transesterification of rapeseed oils for biodiesel production with a novel organic solvent as the reaction medium."

(Continued)

*Primary Examiner* — Yate K Cutliff
(74) *Attorney, Agent, or Firm* — David S. Resnick; Nixon Peabody LLP

(57) ABSTRACT

Disclosed is an enzymatic process for the preparation of fatty acid alkyl esters, particularly fatty acids methyl esters (biodiesel) in a solvent-free microaqueous system, from a fatty acid source and an alcohol or alcohol donor, employing a robust lipase preparation that comprises at least two lipases separately or jointly immobilized on a suitable support, where one of the lipases has increased affinity to partial glycerides, another is sn-1,3 positional specific, and an optional third lipase has high selectivity towards sn-2 position of the glycerol backbone of the fatty acid source.

21 Claims, 4 Drawing Sheets

(56) References Cited

OTHER PUBLICATIONS

Ranganathan et al., Bioresource Technology, 99:3975-3981 (2007). "An overview of enzymatic production of biodiesel."
Salis et al., Journal of Molecular Catalysis B: Enzymatic: 57:262-269 (2008). "Role of the support surface on the loading and the activity of *Pseudomonas fluorescens* lipase used for biodiesel synthesis."
Soumanou et al., Enzyme and Microbial Technology, 33:97-103 (2003). "Improvement in lipase-catalyzed synthesis of fatty acid methyl esters from sunflower oil."
Fjerbaek et al., Biotechnol Bioeng, 102(5):1298-1315 (2009).
Hernandez-Martin et al., Bioresource Technology, 99:277-286 (2008).
Lee et al., J Ind Eng Chem, 12(5):577-782 (2006). "Lipase immobilization on silica gel using a cross-linking method."
Lee et al., Biotechnol Lett, 28:1965-1969 (2006). "Pretreatment of lipase with soybean oil before immobilization to prevent loss of activity."
Noureddini et al., Bioresource Technology, 96:769-777 (2006).
Watanabi et al., J Am Oil Chem Soc, 84:1015-1021 (2007).
Watanabi et al., J Molecular Cat B: Enzymatic, (44):99-105 (2007).
Bryjak J. et al., Chemical Engineering Journal 65:249-256 (1997). "Immobilization of lipase on various acrylic copolymers."
de Oliveira, P.C. et al., ScienceDirect, Biochemical Engineering Journal, 5(1):63-71 (Apr. 2000). "Immobilisation studies and catalytic properties of microbial lipase onto styrene—divinylbenzene copolymer."
Ha, S.H. et al., ScienceDirect, Enzyme and Microbial Technology 41:480-483 (2007). "Lipase-catalyzed biodiesel production from soybean oil in ionic liquids."
Hsu, A. et al. Biotechnol Appl Biochem. 36(Pt 3):181-186 (Dec. 2002). "Immobilized lipase-catalysed production of alkyl esters of restaurant grease as biodiesel."
Nakaoki, T. et al., Industrial Biotechnology, 1(2):126-134 (Summer 2005) doi:10.1089/ind.2005.1.126. "*Candida* antarctica lipase B Catalyzed polymerization of lactones: Effects of immobilization matrices on polymerization kinetics & molecular weight."
Salis, A. et al. J Biotechnol.; 119(3):291-299 (Sep. 29, 2005). "Biodiesel production from triolein and short chain alcohols through biocatalysis."
Watanabe T. et al., Proceedings of 42nd Conv of JP Society of Enzyme Engineering—(1999) p. 63 Engl.

ROBUST MULTI-ENZYME PREPARATION FOR THE SYNTHESIS OF FATTY ACID ALKYL ESTERS

CROSS REFERENCE TO RELATED APPLICATIONS

This application is a 371 National Phase Entry Application of International Application No. PCT/IL2008/001497 filed Nov. 13, 2008, which designates the United States, and is a continuation-in-part, and which claims the benefit of U.S. patent application Ser. No. 11/946,121 filed Nov. 28, 2007, now U.S. Pat. No. 7,790,429 the contents of which are incorporated herein by reference.

FIELD OF THE INVENTION

The invention relates to the preparation of an immobilized multi-enzyme system for transesterification or esterification of oils and fats triglycerides or of fatty acids, with short-chain alcohols, to obtain fatty acid short-chain alkyl esters, preferably to be used as biodiesel. The invention also relates to a process for the preparation of such immobilized multi-enzyme systems, and their various industrial uses in one-step or multi-step processes, particularly for the production of methyl esters, typically used as biodiesel, at approximately complete conversions.

BACKGROUND OF THE INVENTION

Lipases (triacylglycerol hydrolase E.C. 3.1.1.3) are defined as hydrolytic enzymes that act on the ester linkage in triacylglycerol in aqueous systems to yield free fatty acids, partial glycerides and glycerol. This group of enzymes under low water activity is capable of catalyzing their reverse hydrolysis reaction. The reverse catalytic activity of lipases has been widely exploited for the synthesis of valuable compounds that contain ester and amide linkages or other related chemicals containing functional groups such as hydroxyl, carboxylic and amino groups. In particularly, lipases have been utilized for reforming fats, oils, waxes, phospholipids and sphingolipids to obtain new desired functional properties, and for separating optically active compounds from their racemic mixtures. Of particular interest, the use of a multi-enzyme system comprised of different lipases immobilized on a polymeric support will be disclosed for the synthesis of fatty acid short-chain alkyl esters (biodiesel).

Currently, there are more than 40 different lipases and phospholipases commercially available however only a few of them are prepared in commercial quantities. Some of the most industrially promising interfacial enzymes are derived from *Candida antarctica, Candida rugosa, Rhizomucor miehei, Pseudomonas* sp., *Rhizopus niveus, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds, and pancreatin.

The most familiar enzyme immobilization techniques are in general divided according to the following:
1. Physical adsorption of enzymes to solid supports, such as silica and insoluble polymers.
2. Adsorption on ion-exchange resins.
3. Covalent binding of enzymes to a solid support material, such as epoxidated inorganic or polymer supports.
4. Entrapment of enzymes in a growing polymer.
5. Confinement of enzymes in a membrane reactor or in semi-permeable gels.
6. Cross-linking enzyme crystals (CLEC's) or aggregates (CLEA's).

Physical adsorption of lipases based on use of polymeric supports with high porosity or use of ion-exchange resins are the most practiced immobilization methods for lipases. This method is characterized with its simplicity and yielding reliable synthetic activity.

The use of free or immobilized lipases for transesterification of triglycerides and short-chain alcohols to form fatty acid alkyl esters has yielded unsatisfactory results with respect to activity and stability of the enzyme. Also, the cost-effectiveness of the immobilized enzymes, for carrying out enzymatic production of fatty acid alkyl esters at industrial quantities, is still prohibited. Furthermore, it has been reported that all currently available lipases in either their free or immobilized forms are incapable of reaching near to complete conversions, preferably above 99%, for oil triglycerides to fatty acid alkyl esters at reasonable reaction time, particularly below 8 hours.

Another major drawback of lipases results from their low tolerance towards hydrophilic substrates, particularly short-chain alcohols, short-chain fatty acids (both below C4), water and glycerol typically present in the transesterification reaction medium. It has been observed in many research studies that short-chain alcohols and short-chain fatty acids, such as methanol and acetic acid, respectively, are responsible for detaching essential water molecules from the quaternary structure of those enzymes, leading to their denaturation and consequently loss of their catalytic activity. Also, the presence of such hydrophilic molecules in the reaction medium, results in detaching the enzyme molecules from the support and consequently decrease in the enzyme operational lifetime. Therefore, it is not surprising that the application of lipases for production of commercial quantities of fatty acids methyl esters "biodiesel" using oil triglycerides and methanol as substrates is infeasible.

Use of mixtures of lipases has been suggested [Lee, D. H. et al., Biotechnology and Bioprocess Engineering 2006, 11:522-525]. This publication describes production of biodiesel using a mixture of chemically bound, immobilized *Rhizopus oryzae* and *Candida rugosa* lipases. As can be seen, the reaction time was relatively long, typically more than 24 hours to reach conversions over 96% to biodiesel. Also, the results presented in this publication show that the mixture of enzymes used lost more than 20% of its initial activity after as few as 10 cycles of use. This may be attributed to the accumulation of partial glycerides intermediates in the reaction system, which decrease the transesterification reaction and thus prolong the reaction time. The deactivation of the biocatalyst in the system described in this publication is a key drawback, which prevents its industrial application.

It is therefore an object of this invention to provide a new method for obtaining highly active and stable immobilized lipases, particularly for the synthesis of fatty acids alkyl esters, especially fatty acid methyl esters for use as "biodiesel".

It is a further object of the present invention to provide a highly active, and stable, immobilized multi-enzyme preparation which possesses high tolerance towards short-chain alcohols and short-chain fatty acids, especially methanol, ethanol and acetic acid, respectively, and other polyols such as glycerol, as well as other inhibiting factors typically present in oils and fats, in particular of inedible grade.

It is a further object of the present invention to provide a one-step or multi-step enzyme reactor configuration for obtaining the desired product, namely, fatty acid alkyl esters at near to complete conversions during reasonable reaction time, typically below 5 hours.

These and other objects of the invention will become apparent as the description proceeds.

SUMMARY OF THE INVENTION

In a first aspect, the invention relates to a process for the preparation of alkyl esters of fatty acids, preferably short-chain alkyl esters of fatty acids, such as fatty acid methyl esters (biodiesel) in solvent-free microaqueous system comprising providing a fatty acid source, stepwise adding a free alcohol, preferably a short-chain free alcohol, particularly methanol, or any other alcohol donor, to said fatty acid source in the presence of a lipase preparation and allowing the reaction to proceed under suitable conditions, until said fatty acid source triglycerides are converted to fatty acid alkyl esters, preferably fatty acid methyl esters (FAME), wherein said lipase preparation comprises at least two lipases, preferably three lipases, said lipases being separately or jointly immobilized on a suitable support and wherein at least one of said lipases has increased affinity for partial glycerides and at least one of said lipases is sn-1,3 positional specific, and optionally a third lipase having high selectivity towards sn-2 position of the glycerol backbone.

The sn-1,3 positional specific lipase may be selected from the group consisting of *Thermomyces lanuginose, Rhizomucor miehei, Mucor miehei, Pseudomonas* sp., *Rhizopus* sp., *Mucor javanicus, Penicillium roqueforti, Aspergillus niger, Acromobacter* sp. and *Burkholderia* sp., but is not limited thereto. The said lipase having increased affinity for partial glycerides may be selected from the group consisting of *Candida antarctica* B, *Candida antarctica* A, *Candida rugosa, Alcaligenes* sp. and *Penicillium camembertii*, but is not limited thereto. A third lipase may be particularly a lipase having high selectivity towards sn-2 position derived from *Candida antarctica* A or *Pseudozyma* sp.

The fatty acid source used in the process of the invention may comprise at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

The lipases may be jointly immobilized on a suitable support, preferably a hydrophobic aliphatic polymer-based support or a hydrophobic aromatic polymeric support. Each of said lipases may be immobilized on a suitable support, wherein the supports on which the said lipases are immobilized are identical or different.

The support is preferably a porous support, which may be organic or inorganic. Examples of supports are porous inorganic supports, such as, but not limited silica- or and alumina-based supports, and organic supports such as, but not limited to polymeric or polymer-based support, and the supports may optionally contain active functional groups selected from epoxy, aldehyde, or ionic groups.

In the process of this aspect of the invention the conversion of the fatty acid acyl groups or free fatty acids comprised in said fatty acid source to fatty acid methyl esters may be monitored at various time points during the reaction, the reaction medium may be removed by suitable means at any desired time point during the reaction, thereby stopping the reaction, and the formed fatty acid methyl esters and optionally the formed glycerol are isolated from the reaction medium. The reaction may be specifically stopped when the conversion of the fatty acid acyl groups or free fatty acids comprised in said fatty acid source to fatty acid methyl esters has reached at least 70%, preferably at least 85%, more preferably at least 95%.

In a further aspect, the invention relates to a process for the preparation of short-chain alkyl esters of fatty acids, preferably fatty acid methyl esters (biodiesel) in a solvent-free microaqueous system comprising providing a fatty acid source, stepwise adding a short-chain free alcohol, preferably methanol, or any other alcohol donor, to said fatty acid source in the presence of a lipase preparation and allowing the reaction to proceed under suitable conditions, until the conversion of the fatty acid acyl groups or free fatty acids comprised in said fatty acid source to fatty acid methyl esters reaches at least 70% wherein said lipase preparation comprises a single one lipase immobilized on a suitable support, or a mixture of at least two lipases jointly or separately immobilized on a suitable support, while continuously removing the formed glycerol and any excess water from the reaction mixture.

Also in the process of this aspect, the said lipase preparation may comprise at least two lipases, preferably three lipases, said lipases being separately or jointly immobilized on a suitable support. At least one of said lipases has increased affinity for partial glycerides and at least one of said lipases is sn-1,3 positional specific. An optional third lipase preferably has higher selectivity towards sn-2 position than random lipases.

The sn-1,3 positional specific lipase may be, but is not limited to, any one of *Thermomyces lanuginose, Rhizomucor miehei, Mucor miehei, Pseudomonas* sp., *Rhizopus* sp., *Mucor javanicus, Penicillium roqueforti, Aspergillus niger, Acromobacter* sp. and *Burkholderia* sp. The said lipase having increased affinity for partial glycerides may be, but is not limited to, any one of *Candida antarctica* B, *Candida rugosa, Alcaligenes* sp. and *Penicillium camembertii*, and said optional third lipase having higher selectivity towards sn-2 position than random lipases may be, but is not limited to, derived from *Candida antarctica* A and *Pseudozyma* sp.

Also in this process, the fatty acid source may comprise at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

The lipases may be jointly immobilized on a suitable support, preferably a hydrophobic aliphatic polymer-based support or a hydrophobic aromatic polymeric support. Each of said lipases may be immobilized on a suitable support, wherein the supports on which the said lipases are immobilized are identical or different.

The support is preferably a porous support, which may be organic or inorganic. Examples of supports are porous inorganic supports, such as, but not limited silica- or and alumina-based supports, and organic supports such as, but not limited to polymeric or polymer-based support, and the supports may optionally contain active functional groups selected from epoxy, aldehyde, or ionic groups.

Also in the process of this aspect of the invention, the conversion of the fatty acid acyl groups or free fatty acids comprised in said fatty acid source to fatty acid methyl esters may be monitored at various time points during the reaction, the reaction medium may be removed by suitable means at any desired time point during the reaction, thereby stopping the reaction, and the formed fatty acid methyl esters and optionally the formed glycerol are isolated from the reaction medium. The reaction may be specifically stopped when the conversion of the fatty acid acyl groups or free fatty acids comprised in said fatty acid source to fatty acid methyl esters has reached at least 70%, preferably at least 85%, more preferably at least 95%.

In yet another aspect, the invention relates to a solvent-free microaqueous process for the preparation of alkyl esters of fatty acids, preferably short-chain alkyl esters of fatty acids, such as methyl esters (biodiesel) comprising (a) providing a fatty acid source, stepwise adding a short-chain alcohol, preferably methanol, or any other alcohol donor, to said fatty acid source in the presence of a lipase preparation and allowing the reaction to proceed under suitable conditions, until the conversion of the fatty acid acyl groups or free fatty acids comprised in said fatty acid source to fatty acid methyl esters reaches at least 70%, wherein said lipase preparation comprises at least one lipase immobilized on a suitable support, or a mixture of at least two lipases, and preferably three lipases jointly or separately immobilized on a suitable support, while continuously removing the formed glycerol from the reaction mixture, to yield an organic phase containing mainly residual un-reacted glycerides and the formed fatty acid alkyl esters; and (b) reacting the said organic phase with a short-chain free alcohol, preferably methanol, or any other alcohol donor, in the presence of a lipase preparation as defined in step (a) under suitable conditions, until the conversion of the fatty acid acyl groups or free fatty acids comprised in said fatty acid source to fatty acid methyl esters reaches at least 95%.

The lipases, the lipase preparations, the enzyme support, the fatty acid source in the process of this aspect are similar to those used in the other aspects.

Still further, the invention relates to a process for the preparation of a mixture of lipases immobilized on an insoluble support, said mixture comprising a lipase derived from *Candida antarctica* B and at least one lipase derived from *Pseudomonas* sp., *Alcaligenes* sp., *Burhholderia* sp., and *Thermomyces lanuginosa*, the process comprising the steps of (a) contacting a buffer solution containing one of the above lipases and another buffer solution containing the second lipase, or a single buffer solution containing a mixture of the above lipases, with a polymeric support, preferably an ion exchange resin or an adsorbent; more particularly a hydrophobic aliphatic or aromatic polymer-based support, preferably in the presence of a hydrophobic organic solvent, such as n-hexane, added to the immobilization medium at ratios of 1:10 to 10:1 buffer:organic solvent, respectively; (b) mixing the system obtained in step (a) for at least 4 hours at room temperature; (c) filtering off the immobilized lipase mixture, and drying it to a water content of less than 5%.

The insoluble support used in this aspect of the invention is preferably a porous and reticular hydrophobic aliphatic or aromatic polymer-based support, particularly Amberlite XAD 7HP or Amberlite XAD 1600, respectively.

The invention also relates to biodiesel prepared by a process employing the immobilized lipase mixture prepared by the process of the invention.

The said fatty acid short-chain alkyl esters are, in all aspects of the invention, preferably fatty acid methyl, ethyl, iso-propyl or butyl esters (biodiesel).

In a still further aspect, the invention relates to a process for the preparation of fatty acid alkyl esters, preferably fatty acid short-chain alkyl esters, particularly fatty acid methyl esters, in a solvent-free system, comprising providing a fatty acid source, stepwise adding a free alcohol, preferably a short-chain free alcohol, particularly methanol or a higher alcohol, or any other alcohol donor, to said fatty acid source in the presence of a lipase preparation and allowing the reaction to proceed under suitable conditions, until said fatty acid source triglycerides are converted to fatty acid alkyl esters, preferably short-chain alkyl esters, particularly fatty acid methyl esters (FAME), wherein said lipase preparation comprises a first lipase and a second lipase, said lipases being separately or jointly immobilized on a suitable support and wherein said first lipase exhibits higher transesterification activity towards triglycerides compared to its activity towards partial glycerides, and said second lipase exhibits higher transesterification activity towards partial glycerides compared to its activity towards triglycerides, and wherein said two lipases show a synergistic effect in their transesterification activity to obtain the final product.

In yet a further aspect, the invention relates to a process for the preparation of fatty acid alkyl esters, preferably fatty acid short-chain alkyl esters, particularly fatty acid methyl esters, in a solvent-free system, comprising providing a fatty acid source, stepwise adding a free alcohol, particularly a short-chain free alcohol, preferably methanol or a higher alcohol, or any other alcohol donor, to said fatty acid source in the presence of a lipase preparation and allowing the reaction to proceed under suitable conditions, until said fatty acid source triglycerides are converted to fatty acid alkyl esters, preferably fatty acid short-chain alkyl esters, particularly methyl esters (FAME), wherein said lipase preparation comprises a first lipase and a second lipase, said lipases being separately or jointly immobilized on a suitable support and wherein said first lipase releases intermediates in a first transesterification reaction, which are favored by said second lipase for transesterification with an alcohol to form fatty acid alkyl esters.

The invention further relates to a process for the preparation of fatty acid alkyl esters, preferably fatty acid short-chain alkyl esters, particularly fatty acid methyl esters, in microaqueous solvent-free system comprising providing a fatty acid source, stepwise adding a free alcohol, preferably short-chain free alcohol, particularly methanol or higher alcohol, or any other free alcohol or alcohol donor, to said fatty acid source in the presence of a lipase preparation and allowing the reaction to proceed under suitable conditions, until said fatty acid source triglycerides are converted to fatty acid alkyl esters, preferably fatty acid short-chain alkyl esters, particularly methyl esters (FAME), wherein said lipase preparation comprises a first lipase and a second lipase, said lipases being separately or jointly immobilized on a suitable support and wherein said lipases exhibit different substrate specificities that maintain their transesterification activity to triglycerides when used together, while at least one of said two lipases decays in the transesterification reaction medium when used separately with triglycerides as substrate but exhibits high transesterification/esterification activity with partial glycerides and fatty acids as substrates, respectively.

The fatty acid source is at least one of triglycerides, partial glycerides, free fatty acids, phospholipids, esters and amides of fatty acids or a mixture comprised of at least two said sources.

The support may be a reticular hydrophobic polymer comprised of divinylbenzene, or a mixture of divinylbenzene and styrene, and reticular hydrophobic aliphatic polymer comprised of aliphatic acrylic polymers. The support is preferably a porous matrix, of pore size in the range of 25-1000 Å, and preferably in the range of 40-100 Å.

The invention will be described in more detailed on hand of the attached drawings.

Figure 2:
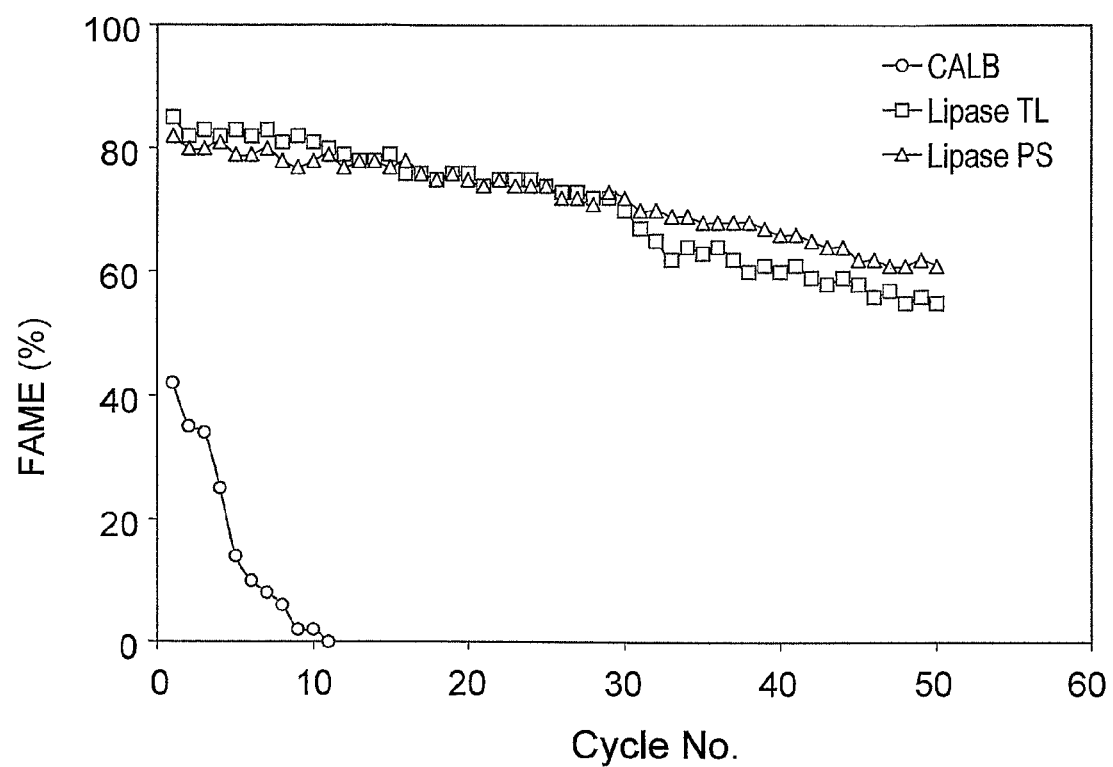

FIG. 2: The transesterification activity of CALB, Lipase PS, Lipase TL all immobilized separately on Amberlite XAD 7HP. Reaction conditions: Soybeans oil (2.5 g) and methanol (3 batches each 91 mg) were mixed with 250 mg immobilized lipase at 30° C. for 6 hours. The same batch of biocatalyst was used in 50 reaction cycles under the same conditions.

Figure 3:
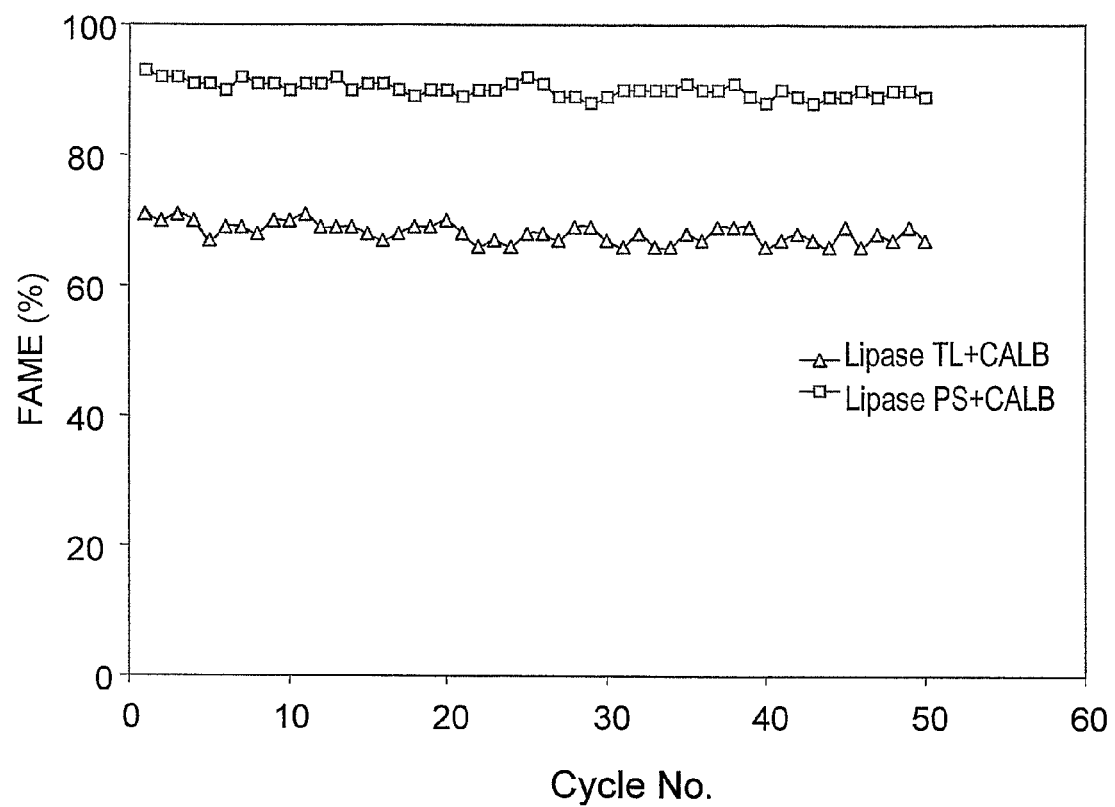

FIG. 3: The transesterification activity of multi-lipase immobilized on Amberlite XAD 7HP for either CALB and lipase TL or CALB and lipase PS. Reaction conditions: Soybeans oil (2.5 g) and methanol (3 batches each 91 mg) were mixed with 250 mg immobilized lipase at 30° C. for 6 hours. The same batch of biocatalyst was used in 50 reaction cycles under the same conditions.

Figure 4:
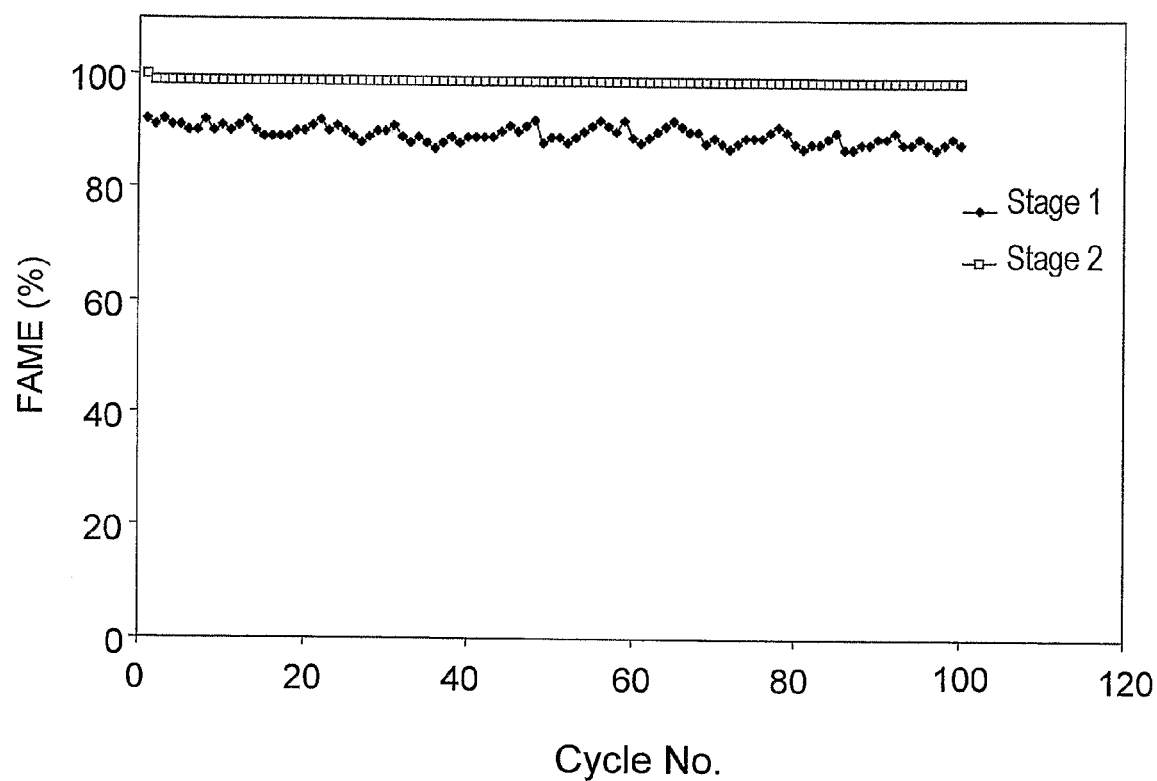

FIG. 4: FAME % in the two-stage transesterification process using lipase PS and CALB both immobilized on Amberlite XAD 7HP. Reaction conditions: The reaction was initiated by adding biocatalyst (30 g) to soybean oil (220 g) and methyl alcohol (23.9 g) into a double-jacketed glass reactor bottomed with a sintered glass filter of porosity of 70-100 µm. The methanol was added in batches each batch is ⅓ of the stoichiometric amount or titrated drop-wise. The reaction system is mechanically stirred at 30° C. for 2 hours. The reaction medium was removed from the first stage, centrifuged to remove glycerol and then introduced to the second-stage reactor and stirred for two hours.

DETAILED DESCRIPTION OF THE INVENTION

In order to improve and facilitate the enzymatic production of biodiesel, the present invention is primarily aimed at preventing enzyme deactivation, or loss of enzyme activity due to detachment of an immobilized enzyme from the support on which it is immobilized, which commonly results from exposure either to methanol, which is one of the starting materials, or from exposure to the glycerol and water formed in the process. The Novozyme 435 lipase (*Candida antarctica* lipase B), immobilized on an adsorbent, which has been used in the past, is characterized with loss of activity after as few as 10 reaction cycles in average, due to the above decay in enzyme activity. It is an aim of the present invention to solve this problem.

Furthermore, in order to reach conversions higher than 96%, the transesterification reaction time of oils and methanol is relatively long, typically in the range of 24-48 hours, with said Novozyme 435 as well as other lipases. It is also an object of the invention to provide a process and enzyme preparations which would considerably shorten the reaction time.

In addition, the glycerol by-product formed in the process leads to decay of the enzyme activity, because it is maintained on the biocatalyst particles. The adherence of glycerol on biocatalysts leads to lowering, or sometimes even total loss of the enzyme activity. The process and preparations of the invention are also aimed at solving this problem.

Further, prior art works used lipases which led to the formation and accumulation of partial glycerides, including mono- and di-glycerides, in the reaction system. Low reaction rates for transesterification of such lipases for those substrates resulted in prolonging the reaction time needed for reaching conversions higher than 96%. The present invention provides for enzymatic preparations, system and process which facilitate a high rate clearance for the intermediates formed in the course of the enzymatic transesterification, and therefore reach high conversions in short reaction times.

More specifically, the invention provides for the use of a multi-enzyme system in one- or two-step processes, which overcomes the above obstacles, yielding unexpected results, and exhibiting synergy between the immobilized enzymes and avoidance of enzyme deactivation or loss of enzyme activity, and also because of efficient combinations of both lipase-lipase and lipase-matrix.

The present inventors have thus developed highly active and stable immobilized enzyme preparations, having high tolerance towards hydrophilic substrates, such as short-chain alcohols, polyols and short-chain fatty acids, for improving enzymatic processes for the production of fatty acid alkyl esters, specifically fatty acid methyl esters "biodiesel". In addition to the above description in the summary of the invention above, the mixture of lipases may also be comprised of more than two lipases, preferably a mixture of three lipases, where a first lipase has sn-1,3 positional specificity, a second lipase has selectivity towards sn-2 position higher than that of random lipases, in particularly random lipases derived from *Candida rugosa*, and a third lipase having increased affinity towards mono- and di-glycerides.

It is to be noted that throughout the application when referring to positions sn-1, sn-2- or sn-3, these are positions on the glycerol backbone of the various glycerides.

The meaning of a lipase having selectivity towards sn-2 position higher than that of random lipases is that such enzyme favors catalyzing the reaction between the alcohol or alcohol donor with the fatty acyl group of the sn-2 position, while random lipases exhibit the same transesterification activity for fatty acyl groups at all three positions on the glycerol backbone.

As will be shown in the Examples below (e.g. with reference to *Candida Antarctica* A (CALA)), some enzymes uniquely exhibit positional activity on sn-2 position, especially under specific conditions determined by the substrates, products, etc. The enzymes used herein in this capacity show distinguished sn-2 positional selectivity and capability to transesterify sn-2 partial glycerides.

The developed biocatalyst is comprised of a mixture of lipases of different types, immobilized on a polymeric matrix, preferably porous, reticular hydrophobic aliphatic or aromatic polymer-based matrix. In accordance with the invention, different lipases may be immobilized in the same reaction pot or separately, on same or different supports. Optionally, different lipases can be immobilized separately on different supports, depending on the best combination enzyme-support with regard to resistance to short-chain alcohols, esterification/transesterification activity and operational life-time for the biocatalyst. The lipase mixture in accordance with the invention comprises a lipase which is sn-1,3 positional specific together with a random lipase, specifically lipase that has affinity to partial glycerides, and optionally a third lipase with a high affinity to the sn-2 position.

The sn-1,3 positional specific lipase may be, but is not limited to *Thermomyces lanuginose, Rhizomucor miehei, Mucor miehei, Pseudomonas* sp., *Rhizopus* sp., *Mucor javanicus, Penicillium roqueforti, Aspergillus niger, Acromobacter* sp. or *Burkholderia* sp. The lipase with specificity towards sn-2 position higher than that of random lipases may be, but is not limited to *Candida antarctica* A lipase and lipase derived from *Pseudozyma* sp. The lipase having increased affinity for partial glycerides may be, but is not limited to *Candida antarctica* B, *Candida rugosa, Alcaligenes* sp. or *Penicillium camembertii*. Other lipases contemplated within the scope of this application may be *Rhizopus niveus, Rhizopus oryzae, Burkholderia* sp., *Chromobacterium viscosum*, papaya seeds or pancreatin.

The immobilization of the different lipases can be carried out either in one pot or separately.

The insoluble support is capable of binding lipases by physical adsorption or by covalent binding to its functional groups. The terms "physically adsorbed" or "physical adsorption" as used herein may be synonymous to "immobilized" and "immobilization", respectively. The terms support and matrix may be used herein synonymously. The support is preferably a hydrophobic porous support which may be organic or inorganic, preferably selected from the group consisting of porous inorganic support such as silica- or alumina-based supports, organic supports such as but not limited to hydrophobic aliphatic and acrylic reticular polymers, or a hydrophobic aromatic reticular polymer-based support, such as Amberlite® XAD 7HP and Amberlite® XAD 1600, respectively, wherein said support may optionally contain active functional groups such as epoxy or aldehyde groups, or ionic groups. Specific non-limiting examples of suitable supports are an Amberlite XAD, such XAD 4, XAD 16, XAD-1600, XAD 7HP, XAD 16HP, XAD 1180, Amberlite FPA53, Amberlite FPC22H, Amberlite FPA4OCl, Amberlite IRC50, a Duolite, such as A7, A561, A568 and Duolite C467, Amberlyst A-21, Dowex Monosphere 77, Dowex Optipore L493, Dow Styrene DVB, MTO Dowex Optipore SD-2, Dowex MAC-3, Purolire A109, and Sepabeads such as EC-EA, EC-EP, EC-BU and EC-OD. Preferred supports are those comprised of hydrophobic reticular aromatic polymers comprised of divinylbenzene, or divinylbenzene and styrene, and hydrophobic aliphatic polymers comprised of reticular aliphatic acrylic polymers.

In a further aspect, the invention provides a process for the preparation of biodiesel, as detailed in the summary of the invention.

Further, in the process for preparing biodiesel in accordance with the invention there may be continuous removal of all or some of the reaction products and/or by-products which are self-desorbed from the enzyme support. The self or spontaneous desorption of the product/by-products off the support carrying the enzyme/s is a unique property of the immobilized enzyme systems of the invention. Without being bound by any particular theory, this feature may be due to the hydrophobic nature of the matrix, which is responsible for repelling the formed hydrophilic glycerol or other hydrophilic substances from the vicinity of the immobilized biocatalyst. The disclosed enzymatic process can be carried out either in one stage or in two stages, in order to reach conversion of the raw materials to their corresponding fatty acid alkyl esters higher than 98%. The novel process of the invention can employ the lipase preparations in accordance with the invention, or a single lipase immobilized on a solid support. In such case, the lipase can be random or sn-1,3-specific, and the combination lipase/support is designed with care, to give a robust and efficient enzyme preparation. The desorbed glycerol is released into the reaction medium and can then be removed out of the system by mechanical means, as described herein. The use of such a system prevents the production of biocatalyst aggregates produced due to adhesion of the beads by the formed glycerol. The formation of enzyme aggregates is one of the key factors responsible for decaying or masking of the enzyme activity, which is overcome by the system and methods of the invention.

In order to reach conversions of raw materials to above 98% two types of process configurations were used:

1. Stirred tank reactor with a bottom sintered glass filter which retains the biocatalyst in the reactor, however allows the reaction medium to permeate through out of the reactor. Such reactor configuration allows the by-product, specifically glycerol, which is self-desorbed from the immobilized enzyme, to sink to the bottom of the reactor, and permeate out through the sintered glass filter. The result is continuous removal of the desorbed formed glycerol and also of excess water, out of the reaction medium, leading to shift of the reaction towards synthesis, thereby reaching conversions above 98%. The biocatalyst used in this reactor may be comprised of a single or multi-types of lipases, in consideration of their positional specificity as well as their origin.

2. Two consecutive stirred tank reactors with a bottom sintered glass filter. A settling tank or centrifuge is used between the two reactors. The first reactor may contain an immobilized biocatalyst comprised of a single or multi-types of lipases. The role of the settling tank or centrifuge between both reactors is to remove the formed glycerol and excess water from the reaction medium, leading to an increase in the conversion of the raw materials to their corresponding fatty acid alkyl esters to above 98% in the second reactor at reasonable reaction time.

In the process of the invention, there is no accumulation of partial glycerides (mono- and di-glycerides) in the system. Such partial glycerides are typically responsible for loss of enzyme activity together with accumulated glycerol. As will be shown in the following Examples, in the process of the invention the biocatalyst activity is unexpectedly retained in repeated use of same enzyme preparation over more than 100 cycles. The reaction time is shortened to less than 4 hours, in comparison to more than 24 hours when other biocatalysts as described in prior art are used in order to reach conversions higher than 96%. These features impart the enzyme preparations and process of the invention with high economic value.

The reaction mixture contained in the thermostated reactor, bottomed with a filter, is reacted under suitable conditions, until the fatty acyl groups or fatty acids are converted to fatty acid alkyl ester, typically fatty acid methyl esters. The reaction medium is filtered through the bottom filter by gravitational force or by applying nitrogen pressure on top of the reactor.

In order to reach conversions higher than 98% at reasonable reaction time, preferably less than 4 hours, the reaction can be carried out at two stages. First, the source of fatty acids is reacted with short-chain alcohol or alcohol donor, such as methanol, for approximately 2 hours where conversions to fatty acid alkyl esters above 70% are obtained. The reaction medium is removed from the reactor bottom maintaining the biocatalyst in the reactor. The reaction medium is allowed to separate into phases or centrifuged in order to remove the formed glycerol. Then, the upper organic phase containing mainly the residual unreacted glycerides and the formed fatty acid alkyl esters is introduced to a second consecutive reactor and allowed to react with methanol in the presence of a lipase or multi-lipase immobilized on a polymeric matrix.

This process yields fatty acid alkyl esters of content higher than 98% and a by-product, namely glycerol, of high quality. The prepared multi-enzyme immobilized preparation is recyclable with insignificant activity losses after reuse in more than 100 cycles.

The reaction of fatty acid sources with an alcohol, such as methanol, or another alcohol donor, to yield biodiesel can also be operated continuously by packing the mixture of the immobilized enzymes in a column and passing the reaction mixture through the column to yield the desired products.

It is to be mentioned that the reactor mode for production of biodiesel, which can be operated batchwise in a stirred-tank reactor, can be also continuously operated, with the biocatalyst being packed in a column.

Solid supports suitable for carrying the lipase/s is/are are described above. Some specific supports are given in the Examples below, particularly in Table 1.

Preferably, a hydrophobic organic solvent, such as n-hexane, can be added to the immobilization medium at ratios of 1:10 to 10:1 buffer:organic solvent, respectively. The immobilized enzymes of the invention prepared by the method of the invention are very active and particularly stable and of high tolerance to hydrophilic substrates, such as short-chain alcohols, short-chain fatty acids and other deactivating enzyme factors typically present in waste oil. Conversions of the fatty acid source of about 90% in the first stage and higher than 98% in the second stage, are retained after even 100 cycles of reaction. This stability is of major economic importance.

Immobilization can be effected in accordance with procedures described in the art. A specifically advantageous method of immobilization is described in applicant's co-pending WO2008/084470 fully incorporated herein by reference. Briefly, the preparation of a lipase immobilized on an insoluble support, is effected by providing a bi-phase system comprised of an aqueous buffer solution and at least one first organic solvent; mixing said interfacial enzyme with the bi-phase system; adding the support to the obtained mixture and mixing; and isolating from the obtained mixture the interfacial enzyme immobilized on said support.

The choice of enzyme is of importance for the efficiency of the enzyme preparation of the invention, particularly for the multi-lipase systems. The combination should be chosen such that decay or loss of activity under the harsh conditions of the reaction is avoided. This can be fulfilled because the bi- or multi-enzyme preparations in the system work synergistically. It is to be understood, that by the term synergism as used herein is also meant the avoidance of enzyme deactivation or decay or loss of enzyme activity. For example, without being bound by theory, some of the transesterification intermediates, mainly monoglycerides and diglycerides, appear to be responsible for the deactivation or decay of the transesterification activity of lipase derived from *Pseudomonas* sp. (herein SP), and lipase derived from *Thermomyces lanuginose* (herein TL). On the other hand lipase derived from *Candida Antarctica* B (herein CALB), has high specificity towards monoglycerides and diglycerides. The presence of CALB and either PS or TL guarantees synergistic effects as defined herein, and thus maintaining the complex biocatalyst with no significant activity loss in repeated use. Furthermore, the presence of an additional, third lipase with high sn-2 affinity, leads to reducing the concentration levels of the formed transesterification reaction intermediates of the type sn-2 acylated glycerol which are characterized by low clearance rate from the reaction medium. Specific combinations of enzymes, and rationale underlying their design will be described in more detail in the following examples. The main point in lipase immobilization within the context of this application is to find the most appropriate matrix to fit the enzyme proteins. This is because possessing high transesterification activity for a specific combination of lipase-matrix does not guarantee the maintenance of the activity in repeated use. The present inventors have established particularly efficient combinations, such as, but not limited to those described herein.

Specifically preferred enzyme combinations are lipase TL and CALB, lipase PS and CALB, lipase TL, CALB and CALA, and lipase PS, CALB and CALA, immobilized on hydrophobic matrices, as described herein.

The use of a two-lipase, or a three-lipase system in accordance with the invention, which possesses high transesterification activity of methanol and oils, and also high stability under the extreme reaction conditions, imparts the developed biocatalyst economic value in the production of biodiesel, with minor costs of the biocatalyst, which can be most efficiently reused.

As will be shown in the following Examples, the enzymatic process for the preparation of fatty acid short-chain alkyl esters in accordance with the invention may employ a first lipase and a second lipase, said lipases being separately or jointly immobilized on a suitable support, with said first lipase exhibiting higher transesterification activity towards triglycerides compared to its activity towards partial glycerides, and said second lipase exhibits higher transesterification activity towards partial glycerides compared to its activity towards triglycerides, said two lipases exhibiting a synergistic effect in their transesterification activity to obtain the final fatty acid alkyl esters product.

In yet another embodiment, the lipase preparation to be used in the process of the invention may comprise a first lipase and a second lipase, said lipases being separately or jointly immobilized on a suitable support, said first lipase releasing intermediates in a first transesterification, reaction, which are favored by said second lipase for transesterification with an alcohol or alcohol donor to form fatty acid alkyl esters.

The alcohol may comprise at least one of methanol, ethanol, iso-propanol, n-butanol, or any other higher alcohol, such as n-hexanol, n-octanol, n-decanol, n-dodecanol, n-tetradecanol, n-hexadecanol and n-octadecanol, or any alcohol donor, or any mixture of at least two thereof. The alcohol donor is preferably a short-chain alkyl carboxylate, such as methyl acetate.

Still further, the lipase preparation may comprise a first lipase and a second lipase, said lipases being separately or jointly immobilized on a suitable support, said lipases exhibiting different substrate specificities that maintain their transesterification activity to triglycerides when used together, while at least one of said two lipases decays in the transesterification reaction medium when used separately with triglycerides as substrate, but exhibits high transesterification/esterification activity with partial glycerides or fatty acids as substrates.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Example 1

Preparation of a Single Lipase Immobilized on a Polymeric Support

Lipase derived from *Thermomyces lanuginosa* ((TL), 1 ml of Lipozyme TL 100 L), or a lipase concentrate derived from *Thermomyces lanuginose*, (Novozymes, Denmark) was solubilized in a TRIS buffer solution (12 ml) of 0.05M and pH 8. The lipase solution was contacted with an enzyme support (1 g, the various supports used are shown in Table 1 below) by shaking or stirring for 8 hours at room temperature. Preferably, a hydrophobic organic solvent, such as n-hexane is added to the immobilization medium at ratios of 1:10-10:1 buffer:organic solvent, respectively. The support containing the immobilized enzyme was filtered off and dried in a desiccator overnight to yield the immobilized lipase. The same procedure was repeated, using either lipase derived from *Pseudomonas* sp. (100 mg Lipase PS, Amano Enzyme, Japan), lipase derived from *Alcaligenes* sp., (50 mg lipase QLM, Meito Sangyo, Japan), *Candida antarctica* lipase A (1 ml of CALA, Novozymes, Denmark) or *Candida antarctica* lipase B concentrate (1 ml, CALB-L, Novozymes, Denmark). These immobilized lipases can be used either separately, in the novel process of the invention, or in combination at different weight ratios in one-pot reaction system or in consecutive two-step or more processes for the preparation of fatty acid alkyl esters (biodiesel) via esterification/transesterification reactions of fatty acid source and alcohol, typically methanol for biodiesel. The reactor mode for production of biodiesel can be operated batchwise in a stirred-tank reactor or continuously where the biocatalyst is packed in a column.

Example 2

Preparation of Multi-Lipase Immobilized Biocatalysts

Lipase derived from *Thermomyces lanuginosa* (1 ml of Lipozyme TL 100 L, Novozymes, Denmark) and *Candida antarctica* B lipase concentrate (1 ml, CALB-L, Novozymes, Denmark) were solubilized in a buffer solution (12 ml) of 0.05M and pH 8. The solution containing both enzymes was contacted with a support, such as Amberlite XAD 7HP or Amberlite XAD 1600, both of Rohm and Haas, USA (1 g) by shaking or stirring for 8 hours at room temperature. Preferably, a hydrophobic organic solvent, such as n-hexane, is added to the immobilization medium at ratios of 1:10-10:1 buffer:organic solvent, respectively. The support containing the immobilized enzymes was filtered off and dried in a desiccator overnight to yield immobilized multi-lipase preparation. The same procedure was repeated, using a solution containing either both lipase PS (100 mg, Amano Enzyme, Japan) and *Candida antarctica* B lipase concentrate (1 ml, CALB-L, Novozymes, Denmark), lipase PS (100 mg, Amano Enzyme, Japan) and *Thermomyces lanuginosa* lipase concentrate (1 ml, CALB-L, Novozymes, Denmark). Other multi-enzyme systems can be prepared, such as, for example, using lipase derived from *Alcaligenes* sp. (50 mg, lipase QLM, Meito-Sangyo, Japan) in combination with either lipase PS or lipase TL. Other lipase preparations might contain three different enzymes in particularly, lipase TL, CAL-A, and CAL-B, or Lipase PS, CAL-A and CAL-B all immobilized on similar or different supports.

Example 3

Preparation of Fatty Acid Methyl Esters (Fame, Biodiesel) Using Immobilized Lipases Table 1 shows the percentage of the formed fatty acid methyl esters (FAME %) in transesterification reaction using lipases derived from *Thermomyces lanuginose* (TL), *Pseudomonas* sp. (PS) and *Candida antarctica* B (CALB), which were each immobilized separately on different supports. Reactions were carried out by adding immobilized lipase (30 g) to soybean oil (220 g) and methyl alcohol (23.9 g) (a stoichiometric ratio of 1:3 between oil triglycerides and methanol, respectively) into a double-jacketed glass reactor bottomed with a sintered glass filter of porosity of 70-100 µm. Methanol was added in batches each batch is ⅓ of the stoichiometric amount or titrated drop-wise. The water concentration in all reaction systems was in the range of 0.1-2%. The reaction system is mechanically stirred at 30° C. Progress of the conversion of the raw materials is determined by measuring the percentage of fatty acid methyl esters, partial glycerides and triglycerides using GC after 8 hours of reaction time under the above mentioned conditions.

Results are given in Table 1, which shows the percentage of the formed fatty acid methyl esters in transesterification system comprised of soybean oil triglycerides (220 g) and methanol (23.9 g) using different, individually immobilized lipases prepared according to Example 1 (30 g). The reaction mixture was mechanically stirred at 30° C. for 8 hours.

TABLE 1

| Immobilized lipase/Type of support | *Thermomyces lanuginosa* lipase FAME (%) | *Pseudomonas* sp. lipase FAME (%) | *Candida antarctica* lipase FAME (%) |
| --- | --- | --- | --- |
| Amberlite XAD 4 | 45 | 55 | 20 |
| Amberlite XAD 16 | 47 | 85 | 55 |
| Amberlite XAD 7HP | 55 | 86 | 40 |
| Amberlite XAD 16HP | 46 | 80 | 40 |
| Duolite XAD 761 | 50 | 85 | 40 |
| Amberlite XAD 1180 | 55 | 87 | 70 |
| Amberlite XAD 1600 | 60 | 80 | 70 |
| Duolite A7 | 65 | 85 | 40 |
| Duolite A561 | 65 | 85 | 75 |
| Duolite A568 | 54 | 80 | 40 |
| Duolite C467 | 75 | 10 | 0 |
| Amberlyst A-21 | 55 | 80 | 40 |
| Dowex monosphere 77 | 40 | 80 | 40 |
| Dowex optipore L493 | 10 | 55 | 0 |
| Dow styrene DVB | 5 | 35 | 5 |
| MTO Dowex optipore SD-2 | 5 | 75 | 5 |
| Dowex MAC-3 | 0 | 0 | 0 |
| Amberlite FPA53 | 45 | 70 | 35 |
| Amberlite FPC22H | 0 | 0 | 0 |
| Amberlite FPA4OCl | 45 | 47 | 45 |
| AmberliteIRC50 | 5 | 15 | 45 |
| Purolire A109 | 45 | 75 | 45 |
| Sepabeads EC-EA | 75 | 85 | 70 |
| Sepabeads EC-EP | 80 | 85 | 75 |
| Sepabeads EC-BU | 85 | 86 | 85 |
| Sepabeads EC-OD | 80 | 85 | 85 |

Example 4

Synthesis of Fatty Acid Methyl Esters (Biodiesel) Using Immobilized Multi-Lipase Preparation Table 2 shows the percentage of the formed fatty acid methyl esters (FAME %) in transesterification reaction using multi-lipase preparation immobilized on Amberlite XAD 7HP comprised of either *Thermomyces lanuginose* (TL) lipase and *Candida antarctica* lipase B (CALB), or *Pseudomonas* sp. (PS) lipase and *Candida antarctica* lipase B, which were immobilized separately, or together on the same support in one-pot system. Also, instead of CALB, a lipase derived from *Alcaligenes*. sp. (Lipase QLM, Meito-Sangyo, Japan) was used in combination with lipases PS or TL. Reactions were carried out by adding immobilized lipase preparation (30 g) to soybean oil (220 g) and methyl alcohol (23.9 g) into a double-jacketed glass reactor bottomed with a sintered glass filter of porosity of 70-100 μm. The methanol was added in batches, each batch being ⅓ of the stoichiometric amount or titrated drop-wise. The reaction system is mechanically stirred at 30° C. Progress of the conversion of the raw materials is determined by measuring the percentage of fatty acid methyl esters, partial glycerides and triglycerides using gas chromatography (GC) after 2, 3 and 6 hours of reaction time under the above mentioned conditions.

The results presented in Table 2 show that lipases TL and PS could not reach FAME at concentration of above 95% after 6 hours of reaction time, while transesterification activity of CALB was relatively low. A multi-lipase immobilized preparation comprised of lipases TL and CALB surprisingly exhibited higher transesterification activity than the control experiments with lipase TL or CALB separately.

As shown in Table 2, the multi-lipase immobilized preparation comprised of lipase PS and CALB exhibited also an improved and synergistic transesterification activity, typically higher than 99%, compared to less than 86% in the control experiments. The same synergistic trend was observed when lipase QLM was used in combination with lipases TL and PS.

Table 2 shows the percentage of the formed fatty acid methyl esters after 2, 3 and 6 hours of reaction time in transesterification system comprised of soybean oil triglycerides (220 g) and methanol (23.9 g) using different multi-lipase mixtures immobilized on Amberlite XAD 7HP, prepared according to Example 2 and also using immobilized lipases prepared according to Example 1 as control experiments. The reaction mixture was mechanically stirred at 30° C. for 6 hours.

TABLE 2

| Immobilized lipase on Amberlite XAD 7HP | FAME (%) After 2 hours | FAME (%) After 3 hours | FAME (%) After 6 hours |
| --- | --- | --- | --- |
| *Thermomyces lanuginose* lipase (control) | 75 | 82 | 85 |
| *Pseudomonas* sp. lipase (control) | 74 | 81 | 86 |
| *Candida antarctica* B lipase (control) | 10 | 18 | 42 |
| *Alcaligenes* sp. Lipase (Lipase QLM) | 52 | 67 | 88 |
| *Thermomyces lanuginosa* and *Candida antarctica* B lipases | 82 | 87 | 96 |
| *Pseudomonas* sp. and *Candida antarctica* B lipases | 82 | 96 | 99.7 |
| *Alcaligenes* sp. and *Thermomyces lanuginosa* Lipases | 71 | 78 | 96 |
| *Alcaligenes* sp. and *Pseudomonas* sp. Lipases | 86 | 98 | 99.5 |

Example 5

Figure 1:
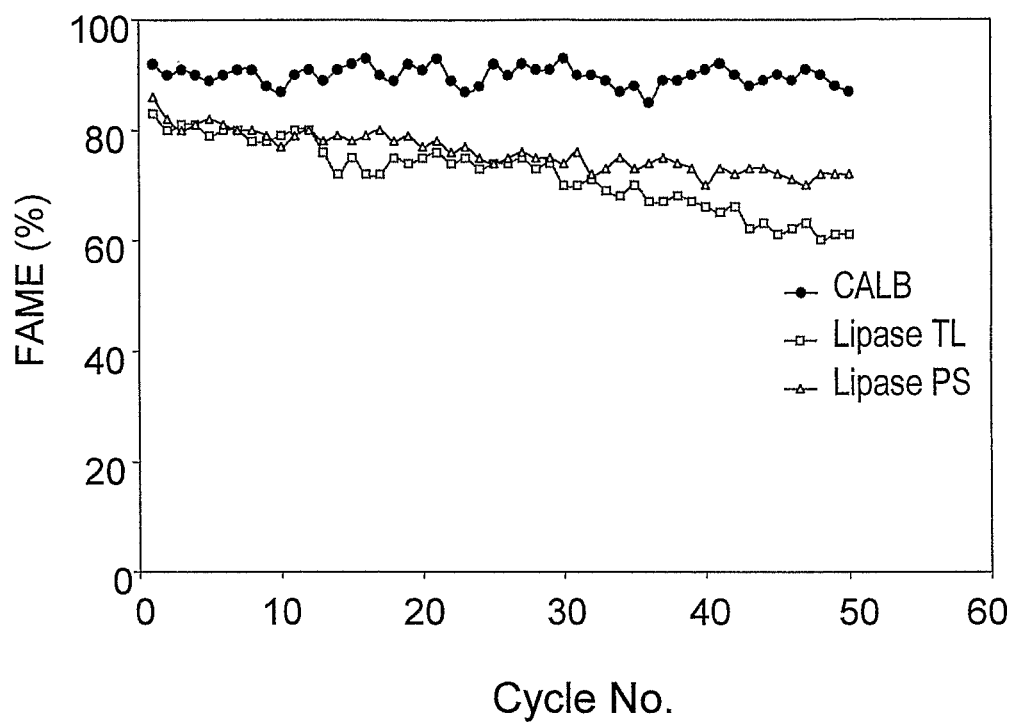
FIG. 1: The esterification activity of CALB, Lipase PS, Lipase TL, each immobilized separately on Amberlite XAD 7HP. Reaction conditions: oleic acid (2.5 g) and methanol (3 batches, each of 95 mg) were mixed with 250 mg immobilized lipase at 30° C. for 6 hours. The same batch of biocatalyst was used in 50 reaction cycles under the same conditions.

Repeated Esterification Activity of the Immobilized Lipases in Batch Reactions Using the Same Batch of Biocatalyst The esterification activity of the biocatalysts was tested by adding one of the three lipases (TL, PS, CALB) immobilized on Amberlite XAD 7HP (250 mg) into a screw-cap vial containing oleic acid (2.5 g) and ⅓ of the stoichiometric amount of methanol (285 mg). The remaining ⅔ of the amount of methanol were added in two equivalent batches, after 2 hours and after 4 hours of reaction time. The composition of the reaction mixture was analyzed after 6 hours. The reaction medium was discarded from the vial and a new batch of fresh substrates was introduced, using the same batch of enzyme. FIG. 1 shows the FAME % in the reaction medium, using the same batch of lipase PS, lipase TL or CALB, each separately immobilized on Amberlite XAD 7HP, in 50 reaction cycles.

The results presented in FIG. 1 show that immobilized CALB, lipases PS and TL preparations all efficiently catalyzed the esterification of free fatty acids and methanol. The repeated esterification activity of CALB was quite stable after 50 reaction cycles while the lipases TL and PS lost linearly 26% and 16% of the initial esterification activity after 50 reaction cycles, respectively.

Example 6

Repeated Transesterification Activity of the Immobilized Lipases in Batch Reactions Using the Same Batch of Biocatalyst The transesterification activity of the biocatalysts in repeated use was tested by adding one of the three lipases immobilized on Amberlite XAD 7HP (250 mg) into screw-cap vial containing soybeans oil (2.5 g) and ⅓ of the stoichiometric amount of methanol (91 mg). The remaining ⅔ of amount of methanol were added in two equivalent batches after 2 hours and after 4 hours of reaction time. The composition of the reaction mixture was analyzed after 6 hours. The reaction medium was discarded from the vial and a new batch of fresh substrates was introduced using the same batch of enzyme.

FIG. 2 shows the transesterification activity of the CALB, lipase PS and lipase TL, separately in 50 reaction cycles using the same batch of biocatalyst. The results show that the transesterification activity of both lipases PS and TL yielded FAME % below 85% and have decayed linearly and reached 70% in average of their initial transesterification activity after 50 reaction cycles. The initial transesterification activity of CALB was relatively low and unexpectedly lost its activity linearly after 11 reaction cycles.

Example 7

Use of Transesterification Activity-Deficient CALB for Esterification Reactions of Fatty Acids and Alcohol CALB immobilized on Amberlite XAD 7HP which has lost its transesterification activity after 11 reaction cycles as described in Example 6 (250 mg) was used for the esterification of oleic acid (2.5 g) and methanol (285 mg). The same batch of biocatalyst was used in 10 reaction cycles. Unexpectedly, the analysis results show that the biocatalyst had a high esterification activity although it lost its transesterification activity in the former experiments. The average FAME % in 10 consecutive runs using the same batch of biocatalyst was 85%.

Example 8

Use of Transesterification Activity-Deficient CALB for Transesterification Reactions of Partial Glycerides and Alcohol CALB immobilized on Amberlite XAD 7HP which has lost its transesterification activity after 11 reaction cycles as described in Example 6 (250 mg) was used for the transesterification of monoolein (3 g) and methanol (270 mg). The same batch of biocatalyst was used in 10 reaction cycles. Unexpectedly, the analysis results show that the biocatalyst had a high transesterification activity for partial glycerides and methanol, although it lost its transesterification activity of triglycerides and methanol in the former experiments. The average FAME % in 10 consecutive runs using the same batch of biocatalyst was higher than 80%.

Example 9

Repeated Transesterification Activity of the Immobilized Multi-Lipase Preparation in Batch Reactions Using the Same Batch of Biocatalyst The transesterification activity of the immobilized multi-lipase preparations were tested by adding either lipase PS and CALB or lipase TL and CALB all immobilized on Amberlite XAD 7HP (250 mg) according to example 1 or 2 into screw-cap vial containing soybeans oil (2.5 g) and ⅓ of the stoichiometric amount of methanol (91 mg). The remaining ⅔ of amount of methanol was added in two equivalent batches after 2 hours and after 4 hours of reaction time. The reaction medium was discarded from the vial after 6 hours of reaction and a new batch of fresh substrates was introduced using the same batch of enzyme. FIG. 3 shows the FAME % in the reaction medium using the same batch of biocatalyst in 50 cycles. The results presented in FIG. 3 show that the transesterification activity of both multi-lipase preparations are unexpectedly stable in 50 reaction cycles using the same batch of biocatalyst.

Example 10

Synthesis of Fatty Acid Methyl Esters (Biodiesel) Using Immobilized Multi-Lipase Preparation in a Two-Step Process Table 3 shows the FAME % in transesterification reaction medium using multi-lipase preparation immobilized on Amberlite XAD 7HP comprised of either lipase TL and CALB, or lipase PS and CALB which were immobilized separately or in a one-pot system. Reactions were carried out by adding immobilized lipase preparation (30 g) to soybean oil (220 g) and methyl alcohol (23.9 g) into a double-jacketed glass reactor bottomed with a sintered glass filter of porosity of 70-100 µm. The methanol was added in batches each batch is ⅓ of the stoichiometric amount or titrated drop-wise. The reaction system is mechanically stirred at 30° C. for 2 hours. When the substrate conversion reached preferably above 70% the reaction medium is filtered from the reactor bottom by applying nitrogen pressure or by its gravitational force over the sintered-glass filter. The reaction medium is either centrifuged or given some time to have phase separation. The bottom phase containing glycerol is removed and the organic phase containing the unreacted glycerides and FAME is introduced to a second consecutive bottomed sintered glass filter containing immobilized lipase. The medium in the second reactor is mechanically stirred with one third of the stoichiometric amount of the initially needed methanol for 2 hours at 30° C. The progress of the reaction was followed by measuring the percentage of fatty acid methyl esters, partial glycerides and triglycerides using GC after 2 hours.

The results presented in Table 3 show that both lipases TL and PS used as control experiments are capable to yield FAME % below 85% in the first step and 98% in the second step while CALB immobilized on Amberlite 7HP exhibited relatively low transesterification activity which did not exceed 15% after the two-step reaction. Multi-lipase preparation comprised of lipase PS and CALB yielded 92% FAME in the first step and 100% in the second step. Similarly, multi-lipase preparation comprised of lipase TL and CALB yielded relatively high FAME % of 90% and near to complete conversion in the second step. The combination of lipases TL and PS yielded high percentage of FAME in the first step and near to complete conversion at the second step. These results support the synergism in transesterification activity of the used lipase combinations described above.

Table 3 shows the percentage of the formed fatty acid methyl esters after 2 hours of reaction time for each step for the transesterification reaction system comprised of soybean oil triglycerides (220 g) and methanol (23.9 g) using different multi-lipase preparation immobilized on Amberlite XAD 7HP prepared according to Example 2. The reaction mixture was mechanically stirred at 30° C. for 2 hours. After phase separation, the upper organic phase was introduced to a second reactor containing immobilized lipase which operates under the same reaction conditions.

TABLE 3

| Step No. | Lipase PS FAME (%) | Lipase TL FAME (%) | CALB FAME (%) | PS/CALB FAME (%) | TL/CALB FAME (%) | PS/TL FAME (%) |
|---|---|---|---|---|---|---|
| Step 1 | 80 | 85 | 5 | 92 | 90 | 85 |
| Step 2 | 98 | 98 | 15 | 100 | 99 | 99 |

Table 3 shows various possibilities for different synergistic enzyme combinations (as can be seen in FIGS. 3 and 4 where multi-enzyme systems were used compared to FIG. 2 where one enzyme was used).

The reaction time is shortened down to 2-3 hours, due to the presence of CALB, responsible for the clearance of the intermediate partial glycerides, namely mono- and di-glycerides, in addition to the clearance of the formed glycerol typically responsible for prolongation of the reaction time and deactivation of the enzyme when only lipase PS or lipase TL are used separately.

Example 11

Synthesis of Fatty Acid Methyl Esters (Biodiesel) Using Immobilized Multi-Lipase Preparation in a Two-Step Process Using the Same Biocatalyst in Consecutive Batches FIG. 4 shows FAME % in stages 1 and 2 for transesterification reaction medium using multi-lipase preparation immobilized on Amberlite XAD 7HP comprised of lipase PS and CALB which were immobilized separately or in one-pot system. Reactions were carried out by adding biocatalyst (30 g) to soybean oil (220 g) and methyl alcohol (23.9 g) into a double-jacketed glass reactor bottomed with a sintered glass filter of porosity of 70-100 µm. The methanol was added in batches each batch is ⅓ of the stoichiometric amount or titrated drop-wise. The reaction system is mechanically stirred at 30° C. for 2 hours. When the substrate conversion reaches preferably above 80% the reaction medium is filtered by nitrogen pressure or by its gravitational force over the sintered-glass filter. The reaction medium is either centrifuged or given some time to have phase separation. The bottom phase containing glycerol was removed and the organic phase containing the unreacted glycerides and FAME is introduced to a second consecutive bottomed sintered glass filter containing the same biocatalyst. The medium in the second reactor is mechanically stirred with one third of the stoichiometric amount of the initially needed methanol for 2 hours at 30° C. The reaction medium is removed from the reactor maintaining the same biocatalyst. This procedure was repeated at least 100 cycles. FIG. 4 shows the FAME % after 2 hours of reaction time in each cycle in the two-stage process. The results in FIG. 4 show that the percentage of FAME after the first stage was approximately 88% in average and reached above 99% in average after the second step. Unexpectedly, the results show that the multi-lipase immobilized preparation is highly active and no significant activity losses were observed in 100 reaction cycles using the same batch of biocatalyst.

Example 12

Production of Biodiesel Using Lipases of Different Substrate Specificity

Table 4 shows the percentage of the formed fatty acid methyl esters after different time intervals for the transesterification reaction of soybean oil triglycerides and methanol using different multi-lipase preparations of various substrate selectivities. The lipases were immobilized according to method described in Example 2 using a porous hydrophobic support, such as Amberlite XAD 1600.

The results presented in Table 4 show that using a multi-enzyme system comprised of a lipase with 1,3-positional specificity such as lipase TL or lipase PS and a lipase with selectivity towards partial glycerides, such as CALB, together with a lipase of high selectivity towards sn-2 position, such as CALA results in significant improvement of the transesterification reaction rate for the production of biodiesel, compared to using similar enzyme preparations however without the addition of a lipase with a high selectivity to sn-2 position, namely CALA.

Table 5 shows the transesterification activity of two multi-lipase preparations comprised of lipase TL, CALB and CALA immobilized either on a porous hydrophobic support, namely Amberlite XAD 1600 or on a porous hydrophilic support such as Duolite A7 both manufactured by Rohm and Haas, USA. The results show that the combination of the above lipases when immobilized on a hydrophobic support yield higher transesterification activity as well much improved operational stability. It can be seen in Table 5 that the biocatalyst comprised of lipases immobilized on a hydrophobic support has maintained its initial transesterification activity with minimal activity loss when the same batch of enzyme was used in 20 consecutive runs, while the transesterification activity using the same lipases however immobilized on a hydrophilic support has decayed substantially, and reached 40% of its initial activity after 20 batches using the same batch of biocatalyst. The results show clearly that hydrophobic supports are favored for the immobilization of lipases to produce biodiesel compared to using of hydrophilic supports for immobilization of the same enzymes.

Table 5 shows the transesterification activity of multi-lipase preparations comprised of lipase TL, CALB and CALA all immobilized either on a porous hydrophobic support, Amberlite XAD 1600, or on a porous hydrophilic support Duolite A7. Reaction conditions: Soybeans oil (2.5 g) and methanol (3 batches each 91 mg) were mixed with 250 mg immobilized lipase preparation at 30° C. for 4 hours. The same batch of biocatalyst was used in 20 reaction cycles under the same conditions.

TABLE 5

| | Biocatalyst | |
|---|---|---|
| Batch No. | Lipase TL, CALB and CALA immobilized on hydrophobic support | Lipase TL, CALB and CALA immobilized on hydrophilic support |
| 1 | 92 | 82 |
| 2 | 91 | 82 |

TABLE 4

The percentage of the formed fatty acid methyl esters after different time intervals for the transesterification reaction system comprised of soybean oil triglycerides (2.5 g) and methanol (285 mg) using different multi-lipase preparations immobilized on Amberlite XAD 1600 (15% wt.) prepared according to Example 2.

| | lipase | | | |
|---|---|---|---|---|
| Time | Lipase PS + CALB | Lipase PS + CALB + CALA | Lipase TL + CALB | Lipase TL + CALB + CALA |
| 1 | 48 | 57 | 43 | 59 |
| 2 | 80 | 86 | 82 | 91 |
| 3 | 94 | 97 | 92 | 98 |
| 4 | 99 | 99.7 | 95 | 99 |

Methanol was added in three equivalent batches during a reaction period of 2 hours. The reaction mixture was shaken and incubated at 30° C. The weight ratios between the different enzyme preparations were 60% PS:40% CALB and 60% PS:20% CALB:20% CALA. Similar weight ratios between TL:CALB and TL:CALB:CALA were used.

TABLE 5-continued

| | Biocatalyst | |
|---|---|---|
| Batch No. | Lipase TL, CALB and CALA immobilized on hydrophobic support | Lipase TL, CALB and CALA immobilized on hydrophilic support |
| 3 | 91 | 75 |
| 4 | 90 | 72 |
| 5 | 90 | 66 |
| 6 | 89 | 65 |
| 7 | 89 | 62 |
| 8 | 90 | 57 |
| 9 | 88 | 55 |
| 10 | 89 | 53 |
| 11 | 88 | 52 |
| 12 | 88 | 50 |
| 13 | 89 | 50 |
| 14 | 89 | 47 |
| 15 | 87 | 44 |
| 16 | 87 | 43 |
| 17 | 88 | 40 |
| 18 | 87 | 39 |
| 19 | 87 | 38 |
| 20 | 87 | 33 |

The invention claimed is:

1. A process for the preparation of alkyl esters of fatty acids in solvent-free microaqueous system comprising: providing a fatty acid triglyceride source, stepwise adding a free alcohol or alcohol donor, to said fatty acid source in the presence of a lipase preparation and allowing the reaction to proceed under suitable conditions, until said fatty acid source triglycerides are converted to fatty acid alkyl esters, wherein said lipase preparation comprises at least three lipases, said lipases being separately or jointly immobilized on a support which is any one of hydrophobic aliphatic polymer-based support and hydrophobic aromatic polymer-based support, and wherein at least one of said lipases has increased affinity for partial glycerides, at least one of said lipases is sn-1,3 positional specific, and at least one of said lipases has high selectivity towards sn-2 position of the glycerol backbone, wherein said sn-1,3 positional specific lipase is selected from the group consisting of *Thermomyces lanuginose, Rhizomucor miehei, Mucor miehei, Pseudomonas* sp., *Rhizopus* sp., *Mucor javanicus, Penicillium roqueforti, Aspergillus niger, Acromobacter* sp. and *Burkholderia* sp., and said lipase having increased affinity for partial glycerides is selected from the group consisting of *Candida antarctica* B, *Candida antarctica* A, *Candida rugosa, Alcaligenes* sp. and *Penicillium camembertii*.

2. The process of claim 1, wherein said lipase having high selectivity towards sn-2 position derived from *Candida antarctica* A or *Pseudozyma* sp.

3. The process of claim 1, wherein said fatty acid source comprises at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

4. The process of claim 1, wherein said lipases are jointly immobilized on said support.

5. The process of claim 1, wherein each of said lipases is immobilized on one said support, and wherein the supports on which the said lipases are immobilized are identical or different.

6. The process of claim 1, wherein said support is a porous hydrophobic support, and wherein said support may optionally contain active functional groups selected from epoxy, aldehyde or ionic groups.

7. The process of claim 6, wherein the reaction is stopped when the conversion of the fatty acid acyl groups or free fatty acids comprised in said fatty acid source to fatty acid alkyl esters has reached at least 70%.

8. A solvent-free microaqueous process for the preparation of short-chain alkyl esters of fatty acids, comprising:
(a) providing a fatty acid triglyceride source, stepwise adding a short-chain alcohol, or any other alcohol donor, to said fatty acid source in the presence of a lipase preparation and allowing the reaction to proceed under suitable conditions, until the conversion of the fatty acid acyl groups comprised in said fatty acid source to fatty acid short-chain alkyl esters reaches at least 70%, wherein said lipase preparation comprises at least one lipase immobilized on a support, or a mixture of at least two lipases, or a mixture of at least three lipases jointly or separately immobilized on a support, wherein each said support is any one of hydrophobic aliphatic polymer-based support and hydrophobic aromatic polymer-based support, while continuously removing the formed glycerol from the reaction mixture, to yield an organic phase containing mainly residual un-reacted glycerides and the formed fatty acid short-chain all esters;
(b) reacting the said organic phase with a short-chain free alcohol, or any other alcohol donor, in the presence of a lipase preparation as defined in step (a) under suitable conditions, until the conversion of the fatty acid acyl groups comprised in said fatty acid source to short-chain alkyl esters of fatty acids reaches at least 95%.

9. The process of claim 8, wherein at least one of said lipases has increased affinity for partial glycerides, at least one of said lipases is sn-1,3 positional specific, and at least one of said lipases has high selectivity towards sn-2 position.

10. The process of claim 8, wherein, said fatty acid source comprises at least one of soybean oil, canola oil, rapeseed oil, olive oil, castor oil, palm oil, sunflower oil, peanut oil, cotton seed oil, Jatropha oil, animal-derived fat, waste cooking oil, oil triglycerides derived from inedible plant sources, or any mixture of at least two thereof.

11. The process of claim 10, wherein said sn-1,3 positional specific lipase is selected from the group consisting of *Thermomyces lanuginose, Rhizomucor miehei, Mucor miehei, Pseudomonas* sp., *Rhizopus* sp., *Mucor javanicus, Penicillium roqueforti, Aspergillus niger, Acromobacter* sp. and *Burkholderia* sp. and said lipase having increased affinity for partial glycerides has low or no transesterification activity for triglycerides and is selected from the group consisting of *Candida antarctica* B, *Candida rugosa, Alcaligenes* sp. and *Penicillium camembertii*, and said optional third lipase having high selectivity towards sn-2 position is selected from the group consisting of *Candida antarctica* A and *Pseudozyma* sp.

12. A process for the preparation of fatty acid short-chain alkyl esters in a solvent-free microaqueous system comprising:
providing a fatty acid triglyceride source, stepwise adding a free short-chain alcohol or short-chain alcohol donor, to said fatty acid source in the presence of a lipase preparation and allowing the reaction to proceed under suitable conditions, until said fatty acid source triglycerides are converted to fatty acid alkyl esters, wherein said lipase preparation comprises a first lipase and a second lipase, said lipases being separately or jointly immobilized on a hydrophobic support which is any one of hydrophobic aliphatic polymer-based support and hydrophobic aromatic polymer-based support and wherein said first lipase exhibits higher transesterification activity towards triglycerides compared to its activity towards partial glycerides, and said second lipase exhibits higher transesterification activity towards partial glycerides compared to its activity towards triglycerides, and wherein said two lipases show a synergistic effect in their transesterification activity to obtain the final product.

13. A process for the preparation of fatty acid short-chain alkyl esters, in a solvent-free microaqueous system, comprising: providing a fatty acid triglyceride source, stepwise adding a free short-chain alcohol, or any other short-chain alcohol donor, to said fatty acid source in the presence of a lipase preparation and allowing the reaction to proceed under suitable conditions, until said fatty acid source triglycerides are converted to fatty acid short-chain alkyl esters, wherein said lipase preparation comprises a first lipase and a second lipase, said lipases being separately or jointly immobilized on a hydrophobic support which is any one of hydrophobic aliphatic polymer-based support and hydrophobic aromatic polymer-based support and wherein said first lipase releases intermediates that are at least one of monoglycerides and diglycerides in a first transesterification reaction polymer-based support, which are favored by said second lipase for transesterification with an alcohol to form fatty acid alkyl esters.

14. A process for the preparation of fatty acid short-chain alkyl esters in solvent-free microaqueous system, comprising:
providing a fatty acid triglyceride source, stepwise adding a free alcohol or alcohol donor, to said fatty acid source in the presence of a lipase preparation and allowing the reaction to proceed under suitable conditions, until said fatty acid source triglycerides are converted to fatty acid alkyl esters, wherein said lipase preparation comprises a first lipase and a second lipase, said lipases being separately or jointly immobilized on a hydrophobic support which is any one of hydrophobic aliphatic polymer-based support and hydrophobic aromatic polymer-based support and wherein said lipases exhibit different substrate specificities that maintain their transesterification activity to triglycerides when used together, while at least one of said two lipases decays in the transesterification reaction medium when used separately with triglycerides as substrate but exhibits high transesterification/esterification activity with partial glycerides and fatty acids as substrates, respectively.

15. The process of claim 1, wherein said alkyl esters are fatty acid short-chain alkyl esters and said free alcohol is a short-chain alcohol.

16. The process of claim 1, wherein said alkyl esters are fatty acid methyl esters (biodiesel) and said free alcohol is methanol.

17. The process of claim 8, wherein said short-chain alkyl esters of fatty acids are fatty acid methyl esters (biodiesel) and said short-chain alcohol is methanol.

18. The process of claim 12, wherein said short-chain alkyl esters of fatty acids are fatty acid methyl esters (biodiesel) and said short-chain alcohol is methanol.

19. The process of claim 13, wherein said short-chain alkyl esters of fatty acids are fatty acid methyl esters (biodiesel) and said short-chain alcohol is methanol.

20. The process of claim 14, wherein said short-chain alkyl esters of fatty acids are fatty acid methyl esters (biodiesel) and said free alcohol is methanol.

21. The process of claim 16, wherein the conversion of the fatty acid acyl groups or free fatty acids comprised in said fatty acid source to fatty acid methyl esters is monitored at various time points during the reaction, the reaction medium is removed by suitable means at any desired time point during the reaction, thereby stopping the reaction, and the formed fatty acid methyl esters and optionally the formed glycerol are isolated from the reaction medium.

\* \* \* \* \*

UNITED STATES PATENT AND TRADEMARK OFFICE
CERTIFICATE OF CORRECTION

Page 1 of 2

PATENT NO.       : 8,617,866 B2
APPLICATION NO.  : 12/744761
DATED            : December 31, 2013
INVENTOR(S)      : Sobhi Basheer et al.

It is certified that error appears in the above-identified patent and that said Letters Patent is hereby corrected as shown below:

In the Claims

Column 22, line 5-39, Claim 8 should read
8. A solvent-free microaqueous process for the preparation of short-chain alkyl esters of fatty acids, comprising:
(a) providing a fatty acid triglyceride source, stepwise adding a short-chain alcohol, or any other alcohol donor, to said fatty acid source in the presence of a lipase preparation and allowing the reaction to proceed under suitable conditions, until the conversion of the fatty acid acyl groups comprised in said fatty acid source to fatty acid short-chain alkyl esters reaches at least 70%, wherein said lipase preparation comprises at least one lipase immobilized on a support, or a mixture of at least two lipases, or a mixture of at least three lipases jointly or separately immobilized on a support, wherein each said support is any one of hydrophobic aliphatic polymer-based support and hydrophobic aromatic polymer-based support, while continuously removing the formed glycerol from the reaction mixture, to yield an organic phase containing mainly residual un-reacted glycerides and the formed fatty acid short-chain alkyl [[all]] esters;
(b) reacting the said organic phase with a short-chain free alcohol, or any other alcohol donor, in the presence of a lipase preparation as defined in step (a) under suitable conditions, until the conversion of the fatty acid acyl groups comprised in said fatty acid source to short-chain alkyl esters of fatty acids reaches at least 95%.

Column 22, line 40, Claim 11 should read
11. The process of claim 9 [[10]], wherein said sn-1,3 positional specific lipase is selected from the group consisting of Thermomyces lanuginose, Rhizomucor miehel, Mucor miehei, Pseudomonas sp., Rhizopus sp., Mucor javanicus, Penicillium roqueforti, Aspergillus niger, Acromobacter sp. and Burkholderia sp. and said lipase having increased affinity for partial glycerides has low or no transesterification activity for triglycerides and is selected from the group consisting of Candida antarctica B, Candida rugosa, Alcaligenes sp. and Penicillium camembertii, and said optional third lipase having high selectivity towards sn-2 position is selected from the group consisting of Candida antarctica A and Pseudozyma sp.

Signed and Sealed this
Twenty-sixth Day of August, 2014

Michelle K. Lee
*Deputy Director of the United States Patent and Trademark Office*

CERTIFICATE OF CORRECTION (continued)
U.S. Pat. No. 8,617,866 B2

Column 24, line 19, Claim 18 should read
18. The process of claim 12, wherein said short-chain alkyl esters of fatty acids are fatty acid methyl esters (biodiesel) and said <u>free</u> short-chain alcohol is methanol.

Column 24, line 22, Claim 19 should read
19. The process of claim 13, wherein said short-chain alkyl esters of fatty acids are fatty acid methyl esters (biodiesel) and said <u>free</u> short-chain alcohol is methanol.

UNITED STATES PATENT AND TRADEMARK OFFICE
CERTIFICATE OF CORRECTION

PATENT NO.       : 8,617,866 B2
APPLICATION NO.  : 12/744761
DATED            : December 31, 2013
INVENTOR(S)      : Basheer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 485 days.

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

Page 1 of 1

PATENT NO.         : 8,617,866 B2
APPLICATION NO.    : 12/744761
DATED              : December 31, 2013
INVENTOR(S)        : Sobhi Basheer, Maisa Haj and Muhammad Kaiyal It is certified that error appears in the above-identified patent and that said Letters Patent is hereby corrected as shown below:

On the title page

Please change item 76 to read as item 75

Item 73 please add Assignee as follows,

TRANS BIODIESEL LTD.
99 HAHISTADRUT AVENUE
C/O L.N. INNOVATIVE TECHNOLOGIES
HAIFA, ISRAEL 32960

Signed and Sealed this
Twenty-second Day of March, 2016

Michelle K. Lee
*Director of the United States Patent and Trademark Office*